United States Patent
Soerens et al.

(10) Patent No.: US 7,378,566 B2
(45) Date of Patent: *May 27, 2008

(54) ABSORBENT CORE INCLUDING FOLDED SUBSTRATE

(75) Inventors: Dave Allen Soerens, Neenah, WI (US); Cathleen Mae Uttecht, Menasha, WI (US); Hoa La Wilhelm, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 352 days.

This patent is subject to a terminal disclaimer.

(21) Appl. No.: 10/318,493

(22) Filed: Dec. 13, 2002

(65) Prior Publication Data

US 2004/0116885 A1    Jun. 17, 2004

(51) Int. Cl.
A61F 13/534 (2006.01)
A61F 13/537 (2006.01)
B32B 3/00 (2006.01)
B32B 5/02 (2006.01)

(52) U.S. Cl. ............ 604/365; 604/359; 604/370; 604/378; 604/385.01; 604/385.201; 442/59; 442/97; 442/99; 442/118

(58) Field of Classification Search ... 604/364–385.01, 604/385.101, 359, 385.201; 442/59, 97, 442/99, 118
See application file for complete search history.

(56) References Cited

U.S. PATENT DOCUMENTS

| | | | |
|---|---|---|---|
| 3,595,235 A | 7/1971 | Jespersen | |
| 3,617,362 A | 11/1971 | Bemmels et al. | |
| 3,699,966 A | 10/1972 | Chapuis | |
| 3,855,046 A | 12/1974 | Hansen et al. | |
| 3,897,784 A * | 8/1975 | Fitzgerald | 604/380 |
| 3,951,893 A * | 4/1976 | Gander | 524/322 |
| 3,959,569 A | 5/1976 | Burkholder, Jr. | |
| 3,963,605 A | 6/1976 | Seabourn | |
| 3,968,798 A | 7/1976 | Hokanson | |
| 4,073,852 A * | 2/1978 | Mesek | 264/122 |
| 4,217,900 A | 8/1980 | Wiegner et al. | |
| 4,232,674 A | 11/1980 | Melican | |
| 4,251,643 A | 2/1981 | Harada et al. | |
| 4,291,136 A | 9/1981 | Keogh | |
| 4,317,449 A | 3/1982 | Nowakoski | |
| 4,328,323 A | 5/1982 | Keogh | |
| 4,333,465 A | 6/1982 | Wiegner | |
| 4,343,917 A | 8/1982 | Keogh | |
| 4,353,997 A | 10/1982 | Keogh | |

(Continued)

FOREIGN PATENT DOCUMENTS

CA    756190    4/1967

(Continued)

*Primary Examiner*—Karin Reichle
(74) *Attorney, Agent, or Firm*—Armstrong Teasdale LLP

(57) ABSTRACT

An absorbent core is provided including a substrate that performs at least one fluid handling function. At least a portion of at least one region of the substrate has been modified by aperturing, calendering, coating, creping, heating, printing, stretching, or a combination thereof to impart at least one different fluid handling function. The substrate is folded to provide a plurality of panels wherein at least a portion of one panel corresponds to at least a portion of the modified region of the substrate. An absorbent article including the absorbent core and a process for making the absorbent core are also disclosed.

29 Claims, 6 Drawing Sheets

U.S. PATENT DOCUMENTS

| | | |
|---|---|---|
| 4,369,289 A | 1/1983 | Keogh |
| 4,381,782 A | 5/1983 | Mazurak et al. |
| 4,408,011 A | 10/1983 | Barnabeo |
| 4,410,324 A | 10/1983 | Sabee |
| 4,434,272 A | 2/1984 | Keogh |
| 4,440,907 A | 4/1984 | Keogh |
| 4,446,279 A | 5/1984 | Keogh |
| 4,459,396 A | 7/1984 | Yamasaki et al. |
| 4,489,029 A | 12/1984 | Keogh et al. |
| 4,493,924 A | 1/1985 | Rifi |
| 4,526,930 A | 7/1985 | Keogh |
| 4,551,504 A | 11/1985 | Barnabeo |
| 4,575,535 A | 3/1986 | Keogh |
| 4,576,596 A | 3/1986 | Jackson et al. |
| 4,578,070 A | 3/1986 | Holtman |
| 4,579,913 A | 4/1986 | Keogh |
| 4,585,449 A | 4/1986 | Karami |
| 4,593,071 A | 6/1986 | Keogh |
| 4,676,784 A | 6/1987 | Erdman et al. |
| 4,676,820 A | 6/1987 | Le Sergent et al. |
| 4,753,993 A | 6/1988 | Keogh |
| 4,921,136 A | 5/1990 | Roggenburg, Jr. |
| 4,940,646 A | 7/1990 | Pawlowski |
| 4,960,477 A | 10/1990 | Mesek |
| 5,035,892 A | 7/1991 | Blank et al. |
| 5,047,476 A | 9/1991 | Keogh |
| 5,057,166 A * | 10/1991 | Young et al. ............. 156/62.2 |
| 5,072,687 A | 12/1991 | Mitchell et al. |
| 5,089,564 A | 2/1992 | Bullen |
| 5,112,919 A | 5/1992 | Furrer et al. |
| 5,145,906 A | 9/1992 | Chambers et al. |
| 5,196,470 A | 3/1993 | Anderson et al. |
| 5,204,404 A | 4/1993 | Werner, Jr. et al. |
| 5,364,382 A | 11/1994 | Latimer et al. |
| 5,389,728 A | 2/1995 | Prejean |
| 5,423,786 A | 6/1995 | Fung et al. |
| 5,429,788 A | 7/1995 | Ribble et al. |
| 5,489,647 A * | 2/1996 | Kussmaul et al. ......... 525/54.3 |
| 5,532,350 A | 7/1996 | Cottrell et al. |
| 5,538,783 A | 7/1996 | Hansen et al. |
| 5,558,832 A | 9/1996 | Noel et al. |
| 5,609,727 A * | 3/1997 | Hansen et al. ............. 162/184 |
| 5,614,570 A | 3/1997 | Hansen et al. |
| 5,635,191 A | 6/1997 | Roe et al. |
| 5,637,106 A | 6/1997 | Mitchell et al. |
| 5,643,588 A | 7/1997 | Roe et al. |
| 5,656,132 A | 8/1997 | Farrington, Jr. et al. |
| 5,730,737 A | 3/1998 | Widlund et al. |
| 5,814,567 A | 9/1998 | Yahiaoui et al. |
| 5,827,254 A | 10/1998 | Trombetta et al. |
| 5,853,867 A | 12/1998 | Harada et al. |
| 5,879,751 A | 3/1999 | Bogdanski |
| 5,885,266 A | 3/1999 | Chihani et al. |
| 5,932,068 A | 8/1999 | Farrington, Jr. et al. |
| 5,932,668 A | 8/1999 | Friebe et al. |
| 5,964,742 A | 10/1999 | McCormack et al. |
| 5,977,014 A * | 11/1999 | Plischke et al. ............ 502/401 |
| 6,020,071 A | 2/2000 | Watson |
| 6,051,317 A | 4/2000 | Brueggemann et al. |
| 6,054,523 A | 4/2000 | Braun et al. |
| 6,060,636 A | 5/2000 | Yahiaoui et al. |
| 6,159,591 A | 12/2000 | Beihoffer et al. |
| 6,222,091 B1 | 4/2001 | Beihoffer et al. |
| 6,235,965 B1 | 5/2001 | Beihoffer et al. |
| H1969 H | 6/2001 | Fell et al. |
| 6,329,565 B1 | 12/2001 | Dutkiewicz et al. |
| H2011 H | 1/2002 | Freiburger et al. |
| 6,342,298 B1 | 1/2002 | Evans et al. |
| 6,376,072 B1 | 4/2002 | Evans et al. |
| 6,403,857 B1 | 6/2002 | Gross et al. |
| 6,417,425 B1 | 7/2002 | Whitmore et al. |
| 6,540,853 B1 * | 4/2003 | Suzuki et al. ............... 156/62.2 |
| 6,596,402 B2 | 7/2003 | Soerens et al. |
| 6,610,793 B1 * | 8/2003 | Soerens et al. ............. 525/404 |
| 6,737,491 B2 * | 5/2004 | Soerens et al. ............. 526/279 |
| 6,790,519 B1 * | 9/2004 | Johnson et al. .......... 428/304.4 |
| 6,822,135 B2 * | 11/2004 | Soerens et al. ............. 604/366 |
| 6,967,261 B1 * | 11/2005 | Soerens et al. ............... 602/48 |
| 7,008,979 B2 * | 3/2006 | Schottman et al. ......... 523/334 |
| 7,294,591 B2 * | 11/2007 | Soerens et al. ............... 442/59 |
| 2002/0090453 A1 | 7/2002 | Muthiah et al. |
| 2003/0149413 A1 | 8/2003 | Mehawej |
| 2004/0019339 A1 * | 1/2004 | Ranganathan et al. ...... 604/367 |
| 2004/0116014 A1 * | 6/2004 | Soerens et al. ............... 442/59 |

FOREIGN PATENT DOCUMENTS

| | | |
|---|---|---|
| EP | 0 506 336 A1 | 9/1992 |
| EP | 649644 A1 * | 4/1995 |
| EP | 748 894 | 12/1996 |
| EP | 0 829 245 A2 | 3/1998 |
| EP | 923 921 | 6/1999 |
| EP | 947 549 | 10/1999 |
| EP | 1 013 291 | 6/2000 |
| EP | 1 050 612 | 11/2000 |
| EP | 0 992 252 A2 | 12/2000 |
| EP | 1 110 525 A1 | 6/2001 |
| EP | 1 199 059 A1 | 4/2002 |
| WO | 99/49826 | 10/1999 |
| WO | 99/57201 | 11/1999 |
| WO | 00/36199 | 6/2000 |
| WO | 00/47153 | 8/2000 |
| WO | 01/05440 | 1/2001 |
| WO | 01/26593 | 4/2001 |
| WO | 01/26596 | 4/2001 |
| WO | 01/34082 | 5/2001 |

* cited by examiner

ABSORBENT CORE INCLUDING FOLDED SUBSTRATE

FIELD OF INVENTION

The present invention relates to an absorbent core that includes a substrate that is folded to provide a plurality of panels at least one of which performs at least one fluid handling function distinct from at least one other panel.

BACKGROUND OF THE INVENTION

Disposable absorbent articles typically include an absorbent assembly constructed from one or more layers of material. Generally, each layer of material is included to provide a distinct fluid handling function within the absorbent article. For example, an absorbent assembly may include a layer of material that promotes rapid intake of body exudates such as urine, menses and/or feces, a layer of material that promotes distribution of body exudates throughout the absorbent assembly, a layer of material that provides absorbent capacity, and/or a layer of material that serves as a barrier to inhibit and/or prevent leakage of body exudates from the absorbent article. Layers of moisture insensitive adhesives are often included in such absorbent assemblies to hold the individual layers in a desired configuration.

Unfortunately, these layered assemblies are generally bulky and do not conform well to the anatomy of the wearer. Additionally, the individual layers may shift relative to each other due to the wearer's movement in use resulting in poor fluid management. As a result, absorbent articles including such layered absorbent assemblies may not perform as intended, may have poor fit and may result in discomfort during use.

Another potential shortfall of these layered absorbent assemblies lies in the complex and inefficient processes need to produce them. Generally, each layer must be produced separately offline using a specific technology and then individually fed into the manufacturing process. These combined layers are then typically cut to the desired shape resulting in material waste and cost inefficiencies.

Personal care product designers have attempted to address various aspects of these problems in a variety of ways. For example, it is known to fold an absorbent composite to provide channels or depressions to receive, distribute and retain body fluids and solid exudates. It is also known to fold an absorbent composite to provide bulk in the central or side portions of the absorbent composite to prevent deformation of the absorbent composite in use and to assist in distributing or directing fluids. Others have utilized designs that reduce waste by cutting an absorbent composite to a particular shape and folding the cut portions into the center or crotch portion of the assembly to provide additional absorbent capacity. In each case the folding of the absorbent composite results in greater bulk in the target area (e.g. the crotch or central region and/or side margins). However, for the purposes of discretion and comfort it is desirable to have as thin an absorbent composite as possible without sacrificing absorbent capacity.

Despite all of these techniques there is still a need for an absorbent core that is thin, durable, structurally stable and performs multiple functions. There is also a need for an absorbent core wherein the layers maintain proper position with respect to adjacent layers. Additionally, there is also a need to reduce the bulk of and/or eliminate some of the non-absorbent structural layers to provide a personal care product having a desired level of fit, comfort and performance that is more efficient and less expensive to produce.

SUMMARY OF THE INVENTION

The present invention provides absorbent articles, such as disposable diapers, training pants, adult incontinence products, sanitary napkins, and the like, that include a folded absorbent core that provides multiple desired fluid handling functions within a single composite. This capability eliminates the need to include additional performance enhancing layers such as surge or wicking layers that add bulk to personal care products.

The absorbent articles of the present invention include a folded absorbent core. Optionally, the folded absorbent core may be positioned intermediate a fluid permeable topsheet and a fluid impermeable backsheet. The absorbent core includes a substrate that performs at least one fluid handling function that has been folded to provide a plurality of panels. The substrate may be folded to provide an absorbent core having one of a variety of suitable cross-sectional configurations that may contribute to the overall functionality of the absorbent core. Suitably, the substrate is a single sheet of material that includes at least one region that has been modified to impart at least one different fluid handling function. The substrate is folded such that at least one panel corresponds to at least one region of the substrate that has been modified. The substrate may be modified by aperturing, calendaring, coating, creping, heating, printing, stretching or combinations thereof. For example, the substrate may be modified by coating and/or adhering a modifying material such as, but not limited to, an absorbent material like superabsorbent material, fibrous material, a binding agent, a fluid and/or menses modifying material, and/or an odor control agent to at least a portion of the substrate. The binding agent may be an absorbent adhesive, a non-absorbent adhesive, a crosslinking agent or a combination thereof. The absorbent material may be attached directly or indirectly to the substrate by a physical bond or a chemical bond. Desirably, the substrate is folded such that at least a portion of the binding agent and/or the absorbent material are enclosed within the absorbent core.

The folded absorbent core may be used to make personal care products such as, for example, diapers, diaper pants, training pants, feminine hygiene products, incontinence products, swimwear garments, bed mats, tissue, wipes, medical articles and the like.

The absorbent core of the invention may be formed by providing a substrate, that performs at least one fluid handling function; modifying at least a portion of one region of the substrate to impart at least one different fluid handling function, and folding the substrate to provide a plurality of panels wherein at least a portion of at least one panel corresponds to at least a portion of the modified region of the substrate. The substrate may be modified by aperturing, calendaring, coating, creping, heating, printing, stretching or the like. The process may further include compressing, densifying, embossing, or shaping the folded absorbent core to provide a better body fit.

With the foregoing in mind, it is a feature and advantage of the invention to provide a thin, durable, structurally stable, and multifunctional absorbent core. It is a further feature and advantage of the invention to provide a personal care product that is thinner, more efficient and less expensive to manufacture compared to conventional personal care products.

BRIEF DESCRIPTION OF THE DRAWINGS

These and other objects and features of this invention will be better understood from the following detailed description taken in conjunction with the drawings, wherein.

DEFINITIONS

Figure 1:
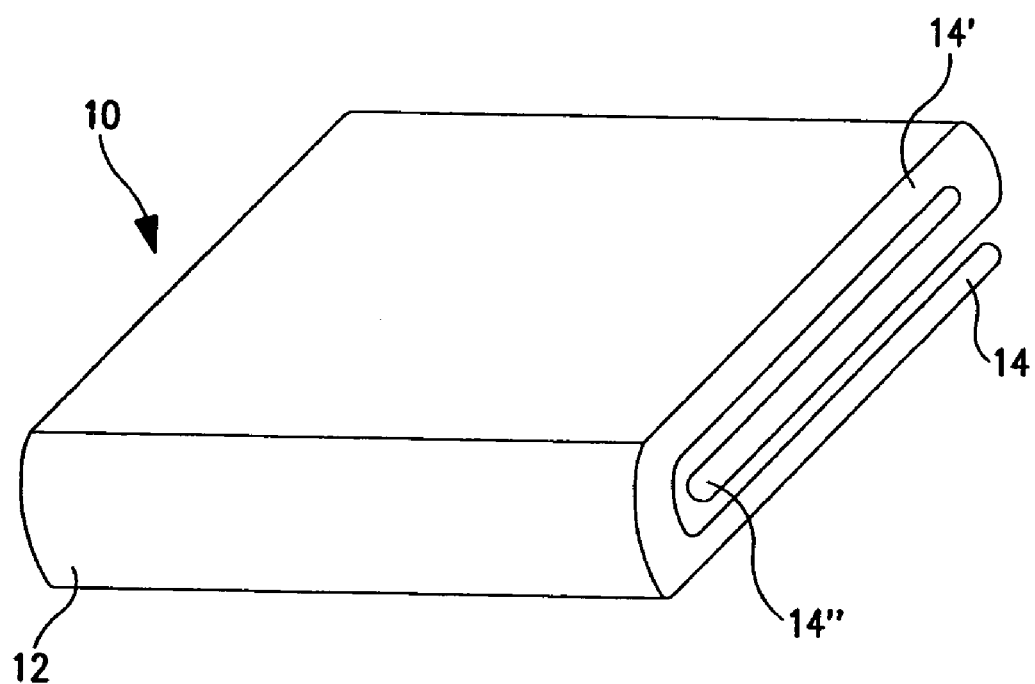
FIG. 1 illustrates a representative folded absorbent core of the present invention.

Within the context of this specification, each term or phrase below will include the following meaning or meanings.

"Attachment mechanism" refers to a mechanism for binding, joining or securing a first material to a second material.

"Binder" or "binding agent" refers to a material having binding, adhesive or attachment properties with or without chemical, thermal, pressure or other treatment.

"Body waste barrier" refers to a fluid handling function wherein a substrate assists in preventing the strikethrough of absorbed body exudates.

"Chemical attachment mechanism" or "chemical bonds" refers to a mechanism for binding, joining or securing a first material to a second material that includes, but is not limited to, hydrogen bonding, covalent bonding, crosslinking such as via an in situ polymerization reaction.

"Cross-sectional profile" refers to a profile created by a plane cutting an absorbent core perpendicular to at least one foldline.

"Desalination" refers to a fluid handling function wherein an electrolyte capable of binding sodium ions is brought into contact with an electrolyte capable of binding chloride ions to reduce the local saline concentration and enhance fluid absorption.

"Distribution" refers to a fluid handling function wherein a fluid is dispersed, wicked, spread, directed or the like within an absorbent core.

"Feminine hygiene products" include sanitary pads and napkins, as well as tampons and interlabial feminine hygiene products.

"Fluid handling function" refers to an attribute of an absorbent core that assists in the collection, transport or absorption of fluids. Such fluid handling functions include, but are not limited to, barrier function, body contact, desalination, distribution, feces containment, feces modification, intake, lock-up, menses containment, menses modification, odor control, retention, and skin treatment.

"Fluid modifying material" includes, but is not limited to, surfactants that change or modify a physical or chemical property of a body exudates such as urine, feces or menses.

"Intake" refers to a fluid handling function wherein a material is capable of capturing a fluid insulted upon an absorbent core.

"Layer", as used herein, includes, but is not limited to, single unfolded sheet or sheets of material, folded sheets of material, strips of material, loose or bonded fibers, multiple sheets or laminates of materials, or other combinations of such materials.

"Lock-up" refers to a fluid handling function wherein a fluid is held within a material and may not be easily given up under pressure.

"Modifying agent" refers to a substance that may be added to a material such as, for example, superabsorbent material, fibers, a substrate, a binding agent, or a fluid to modify a physical or chemical property of the material. For example, a modifying agent may be added to modify the viscosity of the fluid or to affect the fluid permeability of a substrate.

"Multi-functional" refers to a material that may perform two or more fluid handling functions.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Panel", as used herein, includes, but is not limited to, a region or section of a layer wherein at least a portion of the periphery of the region or section is defined by a foldline.

"Personal care product" includes diapers, diaper pants, training pants, swim wear, absorbent underpants, adult incontinence products, feminine hygiene products, and the like.

"Physical attachment mechanism" or "physical bonds" refers to a mechanism for binding, joining or securing a first material to a second material including, but not limited to, heat melting, fiber entangling and adhesive bonding.

"Plurality" means two or more elements or parts such as, for example, an absorbent core including two or more panels.

"Retention" refers to capacity, storage, containment or similar fluid handling function.

"Shape" or "shaping" refers to cutting, heating, molding or similar process used to impart a desired 2- or 3-dimensional configuration to an absorbent core.

"Structurally stable" refers to a material capable of maintaining various elements, layers or components of an absorbent core in position with respect to each other.

"Substrate" refers to a material having a basis weight of about 150 grams per square meter or less, a fluid centrifuge retention capacity of about 10 grains 0.9 weight percent saline per gram material or less and a peak tensile strength under load of at least about 50 grams per centimeter width.

"Superabsorbent" refers to a water-swellable, water-insoluble organic or inorganic material capable, under the most favorable conditions, of absorbing at least about 10 times its weight and, desirably, at least about 20 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

These terms may be defined with additional language in the remaining portions of the specification.

DESCRIPTION OF PREFERRED EMBODIMENTS

The present invention relates to an absorbent core that includes a substrate that is folded to provide a plurality of panels at least one of which performs at least one fluid handling function distinct from at least one other panel. When used in absorbent articles such as disposable diapers, training pants, adult incontinence products, sanitary napkins, and the like, this capability eliminates the need to include additional performance enhancing layers such as surge or wicking layers that add bulk to and affects the performance, fit and comfort of personal care products.

Suitably, the absorbent core has an absorbent capacity of about 5 grams 0.9 weight percent saline per gram composite or more, alternatively of about 10 grams 0.9 weight percent saline per gram composite or more. Desirably, the absorbent core is relatively dense and thus may have a density of at least about 0.5 grams per cubic centimeter, or at least about 0.7 grams per cubic centimeter. Advantageously, the absorbent core is relatively flexible in order to conform more closely to a wearer's body and inhibit and/or prevent leakage when included in a personal care product. Therefore, the absorbent core may have a Gurley stiffness value of about 320 milligrams or less, especially about 160 milligrams or less. Preferably, the absorbent core is also relatively thin in order to provide better fit and comfort when included in a personal care product. Therefore, the absorbent core may have a thickness of about 0.2 to about 4 millimeters.

Referring to FIG. 1, an absorbent core 10 includes a substrate 12 that is folded upon itself to form an absorbent core having a plurality of panels 14. For example, as shown in FIG. 1A, the absorbent core includes three panels, 14, 14' and 14" respectively.

Desirably, the substrate 12 is a single sheet or layer of material that performs at least one fluid handling function (e.g. a base fluid handling function) and may be modified to provide two or more desired fluid handling functions such as, but not limited to, barrier function, body contact, distribution, feces containment, feces modification, intake, lock-up, menses containment, menses modification, odor control, retention, and skin treatment.

The substrate 12 has a basis weight of about 150 grams per square meter or less and a fluid centrifuge retention capacity of about 10 grams 0.9 weight percent saline per gram substrate or less. The substrate 12 is a sheet having a peak tensile strength under load of at least about 50 grams per centimeter width. Suitable substrates 12 include, but are not limited to, nonwoven, woven, and knitted fabrics; cellulosic tissue sheets; plastic films, including polypropylene, low density polyethylene, high density polyethylene, linear low density polyethylene, and ultra low density polyethylene; styrene-ethylene-butylene-styrene or styrene-isoprene-styrene block copolymers, KRATON polymers from Kraton Polymers of Houston, Tex., metallocene catalyzed elastomers or plastomers, and the like or combinations thereof. Other suitable substrates include monolithic breathable films, such as those made of polyether amide based polymers, for example PEBAX available from Atofina Chemical Company of Philadelphia, Pa., and ether/ester polyurethane thermal-plastic elastomers; LYCRA stranded composites; and elastomer net composites.

Figure 2A:
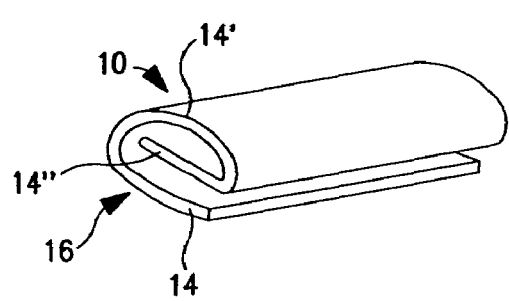
FIGS. 2A through 2F are perspective views of representative absorbent cores of the present invention having various cross-sectional profiles.

The substrate 12 may be folded in any manner in order to provide an absorbent core 10 having at least two panels. Specifically, the substrate 12 may be folded to provide a particular cross-sectional profile. For example, the substrate 12 may be folded to provide at least three panels. In particular, as illustrated in FIG. 2A, the absorbent core 10 has an "e"-shape cross sectional profile 16 including three panels, 14, 14' and 14" respectively. FIG. 2B illustrates an absorbent core 10 having a "z"-shape cross-section 18 including three panels, 14, 14' and 14" respectively. Additionally, FIG. 2C depicts an absorbent core 10 including three panels, 14, 14' and 14" respectively, having a "c"-shape cross-section 20.

Figure 2D:
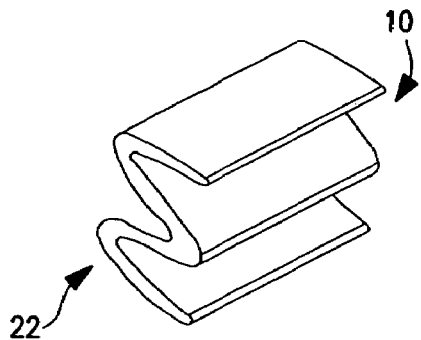
Figure 2B:
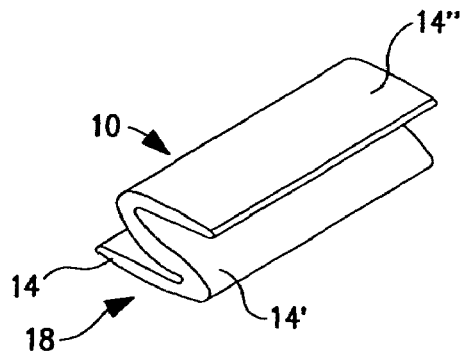
Figure 2E:
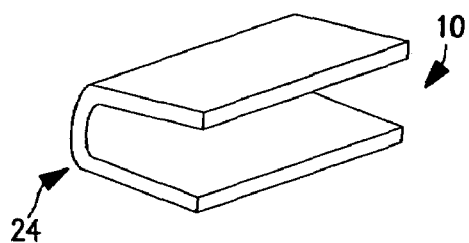
Figure 2C:
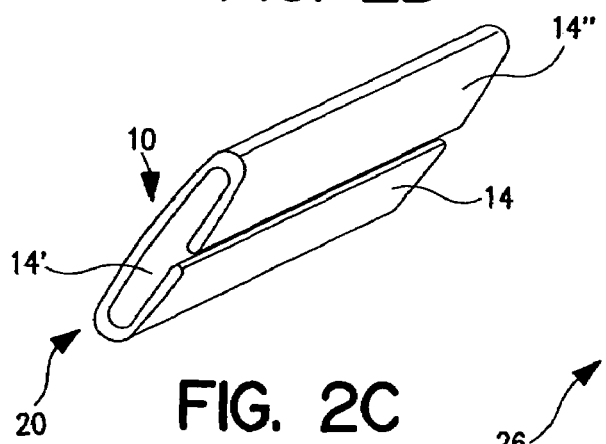
Figure 2F:
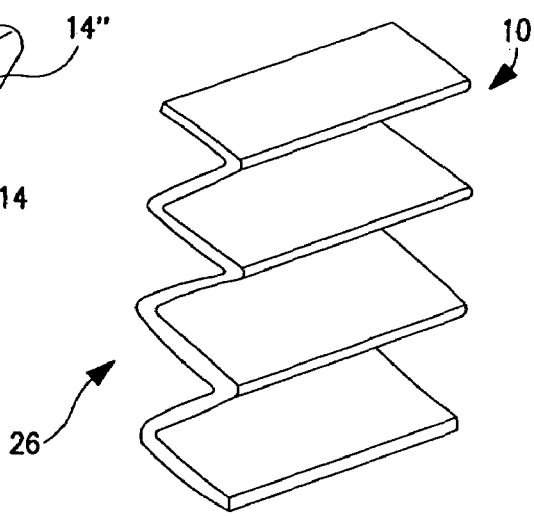

Other suitable cross-sectional profiles are illustrated in FIGS. 2D through 2F. For example, FIG. 2D depicts an absorbent core 10 having a "sigma"-shaped cross-section 22 including four panels. FIG. 2E shows an absorbent core 10 having a "u"-shaped cross-section 24 including two panels while FIG. 2F shows an absorbent core 10 having an "accordion"-shaped cross-section 26 including seven panels. Additionally, the substrate 12 may be folded in any other manner such that the resulting absorbent core 10 includes at least two panels. Suitably, the substrate may be cut, slit, scored, perforated, apertured or the like to facilitate folding.

Figure 3A:
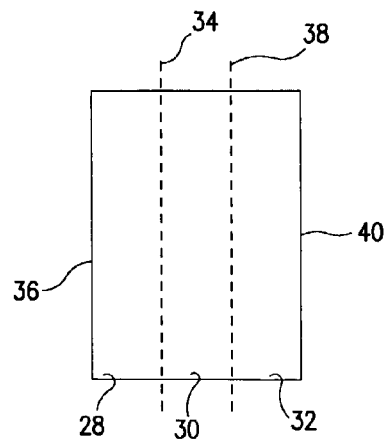
FIGS. 3A through 3C illustrate a method of folding a substrate to provide an absorbent core including a plurality of panels.
Figure 3B:
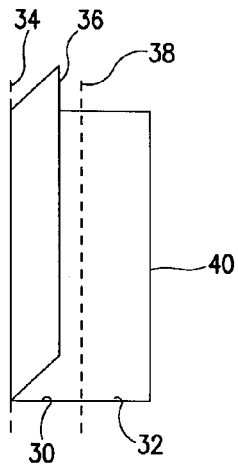
Figure 3C:
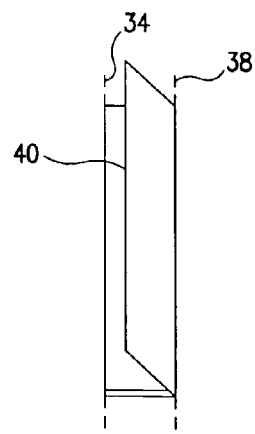

In a representative folding operation, as shown in FIGS. 3A through 3C, the substrate 12 may be folded to form an absorbent core 10 including three panels and having an "e"-shaped cross-section. Referring to FIG. 3A, a substrate 12 including a first region 28, a central region 30 and a second region 32 is folded along a first foldline 34 such that a first edge 36 of the substrate is positioned adjacent a second foldline 38 and the first region 28 overlays the central region 30 as shown in FIG. 3B. As shown in FIG. 3C, the substrate 12 is then folded along the second foldline 38 such that a second edge 40 of the substrate 12 is positioned adjacent the first foldline 34 and the second region 32 overlays the first region 28 to provide an absorbent core 10 having an "e"-shaped cross-section. Alternatively, the substrate 12 could be folded in the reverse order such that the second region 32 overlays the central region 30 and the first region 28 overlays the second region 32 to provide an absorbent core 10 having an "e"-shaped cross-section.

At least a portion of at least one region of the substrate is modified to provide at least one fluid handling function that is different from the base function of the substrate. Suitably, the substrate is folded such that at least one panel of the absorbent core corresponds to at least one modified region of the substrate. For example, a first panel of the absorbent may perform a first fluid handling function as provided by the substrate (e.g. the base fluid handling function) and at least a portion of at least a second panel of the folded substrate may correspond to a region of the substrate that has been modified to perform a different fluid handling function thereby providing a folded absorbent core that performs at least two fluid handling functions. Furthermore, an individual panel may perform more than one fluid handling function. Suitably, each panel of the absorbent core may perform at least one different fluid handling function in order to maximize the utility of the absorbent core.

The desired fluid handling function or functions may be imparted to an individual panel of the absorbent core through a variety of methods. A fluid handling function may be imparted to the substrate by methods including, but not limited to, aperturing, calendering, coating, creping, heating, printing, or stretching at least a portion of the substrate.

In one embodiment, at least a portion of the substrate 12 is coated or treated with a modifying material to impart a desired fluid handling function different than the base function of the substrate and the substrate is folded to provide an absorbent core having at least one panel that corresponds to the modified region of the substrate. Examples of modifying materials include, but are not limited to fluid modifying materials, binding agents, absorbent materials, and odor control agents. More than one modifying material may be coated or applied on the same region or portion of the substrate.

For example, at least a portion of a substrate may be coated or treated with a fluid modifying material such as, for example, a viscoelastant or a surfactant. A "viscoelastant" is an organic agent that, when an effective amount is contacted by a viscoelastic composition, materially alters the properties of that viscoelastic composition, for example, by reducing its viscosity and/or elastic nature. A viscoelastant may be applied to at least a portion of the substrate 12 as a menses modifying material and/or a feces-modifying material.

A suitable viscoelastant for use in the present invention includes an alkyl polyglycoside including 8-10 carbon atoms in the alkyl chain. Alkyl polyglycosides alter the viscoelastic properties of viscoelastic fluids such as menses and feces as well as increase the wettability of synthetic surfaces. One specific viscoelastant suitable for use in the present invention is an alkyl polyglycoside available under the trademark GLUCOPON 220UP from Cognis Corporation of Ambler, Pa.

Other examples of suitable viscoelastants include bovine lipid extract surfactant, available under the registered trademark SURVANTA from Ross Laboratories of Columbus, Ohio, a drug used to treat Acute Respiratory Distress Syndrome and Cystic Fibrosis, and enzymes such as papain and pepsin which cleave protein structures. Some dextrins and dextrans may also be used as viscoelastants. Dextrans (macrose) are polymers of glucose with chain-like structures and molecular weight of, for example, about 200,000 or less produced from sucrose, often by bacterial action. Dextrins (starch gum) are normally solid starch derivatives formed when starch is heated either alone or with nitric acid. A suitable dextran for use in the present invention includes a 4000 MW oligosaccharide available from Polydex Pharmaceuticals, Ltd. of Scarborough, Ontario, Canada.

The addition of the viscoelastant to the substrate may be accomplished by conventional means such as spraying, coating, dipping and the like. Alternatively, in some cases it may be advantageous to add the viscoelastant as an internal additive to the polymer melt used to form the substrate. The amount of viscoelastant applied will depend upon the particular end use as well as factors such as basis weight and porosity of the substrate. Other examples of viscoelastants and methods of application are disclosed in commonly assigned U.S. Pat. No. 6,060,636 to Yahiaoui et al., which is incorporated by reference.

Surfactants may be applied to one or more regions of the substrate 12 in order to improve the fluid permeability or wettability of the substrate, particularly those including substantially hydrophobic materials such as polypropylene, polyethylene, and the like. Suitable surfactants may include amphoteric, anionic, cationic, nonionic, and zwitterionic surfactants. For example, the substrate 12 may be treated with about 0.45 weight percent of a surfactant mixture including AHCOVEL N-62 available from Uniqema Inc., a division of ICI of New Castle, Del., U.S.A. and GLUCOPON 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire substrate 12 or can be selectively applied to particular regions or surfaces of the substrate 12, such as a medial region along a longitudinal centerline or either a top surface or an opposing bottom surface.

In one aspect, at least one region of the substrate may be coated with a binding agent such that when the substrate is folded at least a portion of at least one panel is coated with the binding agent. The binding agent may include an absorbent adhesive composition, a non-absorbent adhesive composition, or a combination thereof. The absorbent adhesive composition may be an in situ neutralizable binder composition, an in situ polymerizable binder composition, a crosslinkable binder composition, or a combination thereof. Absorbent adhesive compositions may be coated onto at least a portion of a substantially non-absorbent substrate such as for example, an apertured film, to provide an absorbent core having intake, barrier and fluid retention functionality. The binding agent may be used alone or in combination with an absorbent material such as superabsorbent, a fluid modifying agent, and/or an odor control agent.

One suitable absorbent adhesive composition may include an absorbent in situ neutralizable binder composition. The absorbent in situ neutralizable binder composition may include a copolymer of an unneutralized polyacid and a polyamine binder material. The unneutralized polyacid may be selected from poly(acrylic acid), poly(methacrylic acid), poly(maleic acid), carboxymethyl cellulose, alginic acid, poly(aspartic acid), and poly(glutamic acid). Suitably, the polyacid includes poly(acrylic acid). The polyamine binder material may be selected from poly(vinylamine), a polyethylenimine, a poly(vinylguanidine), a poly(allylamine), a poly(allylguanidine), a poly(lysine), a poly(arginine), a poly(histidine), a poly(dialkylaminoalkyl (meth)acrylamide) and copolymers containing lysine, arginine, and histidine. Suitably, the polyamine binder material includes poly(vinylamine).

Figure 4A:
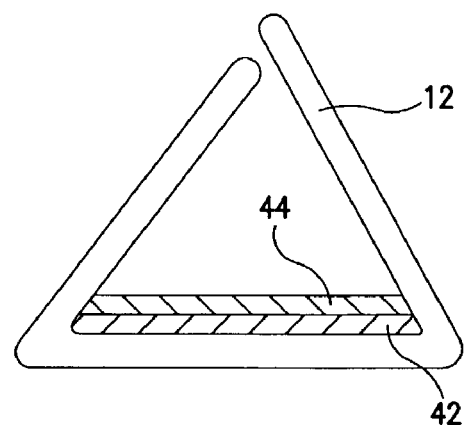
FIGS. 4A through 4C illustrate representative absorbent cores of the present invention including an absorbent in situ neutralizable binder composition.
Figure 4B:
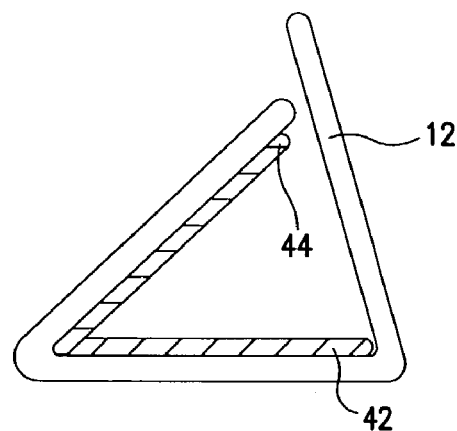
Figure 4C:
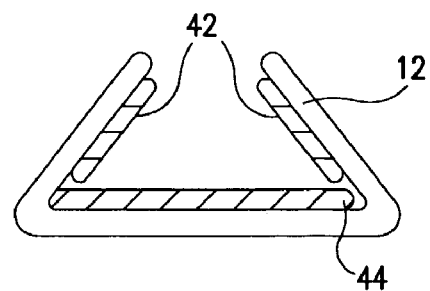

Desirably, the copolymer of an unneutralized polyacid and the polyamine binder material are coated onto the substrate 12 as one or more separate layers. For example, referring to FIGS. 4A through 4C, one or more layers of a copolymer of an unneutralized polyacid 42 are coated onto the substrate 12 and one or more layers of the polyamine binder material 44 are coated onto the same or different portions of the substrate such that when the substrate 12 is folded layer or layers 42 and 44 are brought together. Without wishing to be bound by theory, it is believed that providing a copolymer of an unneutralized polyacid together with a polyamine binder material forms a macro bipolar absorbent film that is capable of desalinating an electrolyte-containing fluid. Desalinating the electrolyte-containing solution is believed to aid in fluid absorption and retention within the absorbent core 10, especially when the absorbent adhesive composition includes a superabsorbent material, by inhibiting or preventing a salt poisoning effect which may reduce the capacity of the absorbent adhesive composition and/or the superabsorbent material. The layers 42 and 44 may be applied to the substrate 12 in any configuration that brings layer 42 together with layer 44. For example, the layer 42 may be brought into direct contact with layer 44. Alternatively, a third layer, such as a nonionic, liquid permeable membrane or an open structure such as a screen can be used as a mediator to allow the reaction between layer 42 and layer 44 to occur.

Another suitable absorbent adhesive composition includes an in situ polymerizable binder composition. One suitable in situ polymerizable binder composition is disclosed in U.S. Pat. No. 6,417,425 to Whitmore et al. which is hereby incorporated by reference. The in situ polymerizable binder composition may be prepared as a sprayable aqueous solution containing a superabsorbent forming monomer and an initiator. Suitable superabsorbent forming monomers include monoethylenically unsaturated compounds (or compounds having a polymerizable double bond) having at least one hydrophilic radical such as carboxyl, carboxylic acid salt, sulfonic acid, sulfonic acid salt, hydroxyl, ether, amide, amino or quaternary ammonium salt groups. Suitable initiators include redox initiators and thermal initiators. Examples of suitable initiators systems may found in U.S. Pat. No. 4,497,903 to Yamasaki et al. and U.S. Pat. No. 5,145,906 to Chamber et al., the disclosures of which are hereby incorporated by reference. The in situ polymerizable binder composition may be applied to a substrate and thereafter is subjected to conditions under which the superabsorbent forming monomers will polymerize. Such condition may include, for example, subjecting the in situ polymerizable binder composition to heat, ultraviolet radiation, e-beam radiation, or a combination thereof. After the superabsorbent forming monomers have been polymerized the coated substrate may be dried to remove any remaining water.

An additional absorbent adhesive composition suitable for use in the present invention includes an absorbent crosslinkable binder composition. The absorbent crosslinkable binder composition may include soluble polymers such as hydrophilic polymers, or blends of hydrophilic polymers or hydrophobic polymers containing hydrophilic agents. Suitably, the crosslinkable binder composition may include a latent crosslinker composed of multivalent metal ions. An example of a suitable binder includes an alkoxysilane grafted poly(ethylene oxide) ("gPEO") that is soluble in alcohol solvents that do not substantially swell or dissolve superabsorbent material. As used herein, the term "substantially swell" refers to a substance that causes a particle to swell, thereby increasing in volume by at least 10 percent. More specifically, the gPEO, upon exposure to moisture, crosslinks into a gel structure capable of absorbing relatively large amounts of fluids, such as water or saline. This type of binder is capable of crosslinking during the solvent drying or evaporating process to provide enhanced wet attachment. Methacryloxypropyl trimethoxy silane is one example of a suitable alkoxysilane grafting monomer.

Water-soluble polymers useful in the present invention include, but are not limited to, poly(alkylene oxides), such as poly(ethylene oxide) ("PEO"), poly(ethylene glycols), block copolymers of ethylene oxide and propylene oxide, poly(vinyl alcohol) and poly(alkyl vinyl ethers). These water-soluble polymers must be capable of graft polymerization with an organic moiety containing a trialkoxy silane functional group or a moiety that reacts with water to form a silanol group. The preferred water-soluble polymer for use in the present invention is PEO.

Other suitable binders include monoethylenically unsaturated carboxylic, sulphonic or phosphoric acids, or salts thereof, and an acrylate or methacrylate ester that contains an alkoxysilane functionality which, upon exposure to water, forms a silanol functional group which condenses to form a crosslinked polymer.

The binders used in the invention should provide very flexible coatings and should therefore have a glass transition temperature of about 30 degrees Celsius or lower, or about 10 degrees Celsius or lower, as measured by a Differential Scanning Calorimeter (DSC). The crosslinkable binder composition desirably has a bending modulus lower than the bending modulus of the substrate.

Organic monomers capable of graft polymerization with PEO or co-polymerization with monoethylenically unsaturated carboxylic, sulphonic or phosphoric acid or salts thereof, which monomers contain a trialkoxy silane functional group or a moiety that reacts with water to form a silanol group, are useful in the practice of this invention. The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, are effective monomers for copolymerization in accordance with the present invention.

The amount of organic monomer having trialkoxy silane functional groups or silanol-forming functional groups relative to the amount of PEO may range from about 0.1 to about 20 weight percent of monomer to the weight of PEO. Desirably, the amount of monomer should exceed 0.1 weight percent in order to sufficiently improve the processability of the PEO. Typically, the monomer addition levels are between about 1.0 percent and about 15 percent of the weight of the base PEO resin; particularly, between about 1.0 percent and about 10 percent of the weight of the base PEO resin; especially, between about 1.5 percent and about 5.5 percent of the weight of the base PEO resin for some intended uses. Suitably, the grafting level may be in the range of 0.5 to about 10 weight percent relative to the weight of the PEO.

The amount of organic monomer having trialkoxy silane functional groups or silanol-forming functional groups relative to the weight of a crosslinkable binder composition including a monoethylenically unsaturated carboxylic, sulphonic or phosphoric acid or salts thereof may range from about 0.1 to about 15 weight percent. Desirably, the amount of monomer should exceed 0.1 weight percent in order to provide sufficient crosslinking upon exposure to moisture. Typically, the monomer addition levels are between about 1.0 percent and about 15 percent of the weight of the polymeric binder composition; particularly, between about 1.0 percent and about 10 percent of the weight of the polymeric binder composition; especially, between about 1.5 percent and about 5.5 percent of the weight of the polymeric binder composition for some intended uses.

Optionally, the polymeric binder may include long chain, hydrophilic monoethylenically unsaturated esters, such as poly(ethylene glycol) methacrylate having from 1 to 13 ethylene glycol units, particularly, between 2 and 10 ethylene glycol units; especially, between 3 and 6 ethylene glycol units.

Suitable acrylic acid salts for use in combination with poly(ethylene glycol) methacrylate include sodium acrylate, potassium acrylate, ammonium acrylate, and quaternary amine acrylate.

The amount of monoethylenically unsaturated hydrophilic esters relative to the weight of the polymeric binder composition thereof may range from about 0 to about 75 weight percent of monomer to the weight of the polymeric binder composition. Typically, the monomer addition levels are between about 10 percent and about 60 percent of the weight of the polymeric binder composition; particularly, between about 20 percent and about 50 percent of the weight of the polymeric binder composition; especially, between about 30 percent and about 40 percent of the weight of the polymeric binder composition for some intended uses.

Crosslinking of the binder is induced after the crosslinkable binder composition has been applied to the substrate. Crosslinking may be induced by a variety of techniques including thermal initiation, radiation initiation, redox chemical reactions, multivalent metal ions, and moisture. Various types of effective radiation initiation include ultraviolet, microwave, and electron-beam radiation. Moisture initiation may be accomplished through hydrolysis and condensation. Multivalent metal ions can initiate crosslinking by complexation. After inducing crosslinking of the binder, the solvent (if present) can be removed from the substrate, either by drying the substrate or using any other effective technique to evaporate the solvent.

Alternatively, one or more regions of the substrate 12 may be coated with a non-absorbent adhesive composition. The non-absorbent adhesive composition may be used to form a fluid barrier on one or more surfaces of the substrate, may be used to bind another material such as an absorbent material to the substrate, or may be used to secure the substrate in a folded configuration. Suitable non-absorbent adhesive compositions, which can be applied continuously or intermittently as beads, a spray, parallel swirls, or the like, can be obtained from Findley Adhesives, Inc., of Wauwatosa, Wis., or from National Starch and Chemical Company, Bridgewater, N.J. Another suitable non-absorbent adhesive composition includes a latex based adhesive.

In another aspect, at least a portion of the substrate 12 may be treated or coated with or may contain an absorbent material. Suitably, the absorbent material has an absorbent capacity of about 7 grams 0.9 weight percent saline per gram absorbent material or more. One such absorbent material includes superabsorbent material.

The superabsorbent material may be of any suitable chemistry to provide absorbency under anticipated usage conditions. Suitable chemistries include crosslinked forms of sodium polyacrylate, sodium polymethacrylate, polyacrylamide, carboxymethyl cellulose, grafted starch, poly(sodium aspartate), poly(vinyl amine), poly(dimethyldiallyl amine), chitosan salt, and/or poly(ethylene imine). Superabsorbent materials are available from various commercial vendors, such as Dow Chemical Company located in Midland, Mich., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water. The superabsorbent material may be present in the absorbent core 10 in an amount of about 95 weight percent or less based on the weight of the absorbent core.

Particle size and geometry of the superabsorbent material may be whatever is suitable for a particular means of applying the superabsorbent material to the substrate 12. For example, the superabsorbent material may be spherical, platelet-like, fibrous, or any related geometry. In the unswollen state, the superabsorbent material may have cross-sectional diameters in a range from about 50 to about 800 microns, or from about 200 to about 400 microns, and for some printing applications from about 60 to about 80 microns, as determined by sieve analysis according to the American Society for Testing Materials (ASTM) Test Method D-1921. Alternatively, the superabsorbent material may be formed on the substrate via an in situ polymerization reaction. It is understood that the particles of material falling within these ranges may include solid particles, porous particles, or may be agglomerated particles including many smaller particles agglomerated into particles within the described size ranges.

Suitably, an attachment mechanism for securing the absorbent material to at least one region of the substrate is provided. Such attachment mechanism includes, but is not limited to, physical bonds, chemical bonds and combinations thereof.

Desirably, the substrate 12 is folded such that at least a portion of modifying material, e.g. the fluid-modifying material, the binding agent or the absorbent material, is enclosed within the absorbent core 10. This is desirable to prevent leakage or seepage of fluid or the modifying material from the absorbent core 10.

The modifying material may be applied to the substrate using any suitable application process, including knife over roll coating, or roll coating, either in a continuous coverage or a patterned coverage. Printing applications are other suitable application techniques, including gravure printing, screen, and jet printing.

In another embodiment, at least a portion of at least one region of substrate 12 is physically modified to impart a desired fluid handling function different to the base function of the substrate and the substrate is folded to provide an absorbent core having at least one panel that corresponds to the modified region of the substrate. Examples of physical modifications of the substrate include, but are not limited to, aperturing, calendering, creping, heating or stretching at least a portion of the substrate.

For example, a portion or region of a substrate such as a cellulosic tissue web can be modified by forming a plurality of apertures. The cellulosic tissue web may then be folded to provide a plurality of panels wherein at least a portion of one panel corresponds to the apertured region. Suitably, the substrate is folded in such a manner that the apertured panel forms at least a portion of one of an opposing top or bottom surface of the absorbent core in order to provide fluid access to the apertures. The resulting absorbent core would perform at least two fluid handling functions: distribution (the base function provided by the substrate); and intake provided by the apertured panel of the absorbent core.

Similarly, at least a portion or region of a film such as thermoplastic film including polyethylene, polypropylene or the like may be modified to provide a plurality of apertures and may thereafter be folded to provide an absorbent core having a plurality of panels wherein at least one panel corresponds to the apertured region of the film substrate. Suitably, the substrate is folded in such a manner that the apertured panel forms at least a portion of one of an opposing top or bottom surface of the absorbent core in order to provide fluid access to the apertures. The resulting absorbent core would perform at least two fluid handling functions: barrier function (the base function of the substrate) and intake provided by the apertured panel of the absorbent core.

In another aspect, at least a portion of a substrate such as nonwoven material may be calendered to provide at least one region having a different density than the uncalendered portion or portions of the substrate. The substrate may thereafter be folded to provide an absorbent core having a plurality of panels wherein at least one panel corresponds to at least a portion of the modified region of the substrate. The resulting absorbent core would perform at least two fluid handling functions: intake (the base function of the substrate) and distribution provided by the calendered or densified panel of the absorbent core.

In any of the preceding embodiments, the substrate may be modified by both coating a region of the substrate with a modifying agent and physically modifying the same or a different region of the substrate region. The resulting modified substrate may be folded in any manner appropriate to provide an absorbent core having a plurality of panels wherein at least one panel corresponds to at least one modified region of the substrate.

A process for making an absorbent core 10 of the present invention includes: providing a substrate that performs at least a first handling function; modifying the substrate by aperturing, calendering, coating, creping, heating, printing, stretching or a combination thereof at least one region of the substrate to impart at least one different fluid handling function; and folding the substrate to provide a plurality of panels such that at least a portion of at least one panel corresponds to the modified region of the substrate.

The process for making the absorbent composite 10 may optionally include the steps of cutting, embossing, bonding, pressing and/or shaping the folded substrate to impart additional fluid handling functionality and/or aesthetic properties to the absorbent composite 10. For example, the folded substrate 12 may be embossed with one of a number of discreet bond patterns. One example of a pattern is the Hansen and Pennings or "H&P" pattern as taught in U.S. Pat. No. 3,855,046 to Hansen and Pennings. Another typical embossing pattern is the expanded Hansen and Pennings or "EHP". Other common patterns include a "Ramisch" diamond pattern with repeating diamonds and an "S" weave pattern as described in commonly assigned U.S. Pat. No. 5,964,742 to McCormack et al., which is incorporated by reference. Additional patterns include, for example, cross directional lines, machine directional lines or other extensible patterns known in the art. One such extensible pattern suitable for use in the present invention is known as "wire weave".

The absorbent core 10 of the invention can be incorporated into any suitable absorbent article. Furthermore, the absorbent core 10 may be positioned or oriented within the absorbent article in any manner that provides the desired fluid handling properties. The absorbent core 10 of the invention is particularly suitable for absorbing liquids such as urine, menses, feces, or sweat, or gases, especially malodorous gases. Examples of absorbent articles that may include an absorbent core 10 include absorbent garments such as training pants, diapers, diaper pants, feminine hygiene products, swimwear, incontinence products, other personal care or health care garments, including medical garments, or the like and absorbent products such as wipes, tissues, underarm sweat pads and bed mats or pads. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. As used herein the term "feminine hygiene product" includes sanitary pads and napkins, as well as tampons and interlabial feminine hygiene products.

Desirably, absorbent articles including an absorbent core 10 of the present invention should have an average thickness of about 6.4 millimeters or less. Furthermore, the structural components of an absorbent article including an absorbent core 10 of the present invention suitably have a thickness of between about 0.2 and about 4 millimeters (mm), or between about 0.5 and about 3.0 mm, or between about 1.0 and about 2.5 mm, as measured at 0.05 pounds square inch (psi) (0.34 kPascals), and an absorbent capacity of between about 0.1 and about 1.8 g/cm$^2$, or between about 0.5 and about 1.4 g/cm$^2$, or between about 0.7 and about 1.1 g/cm$^2$ under an applied load of 0.3 psi (2.07 kPascals). The absorbent capacity of the material can be measured according to the test method described in detail below.

Figure 5A:
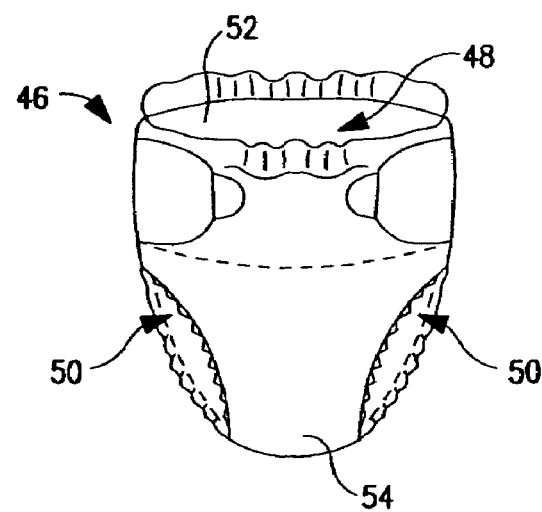
FIGS. 5A and 5B illustrate representative diapers including an absorbent core of the present invention.
Figure 5B:
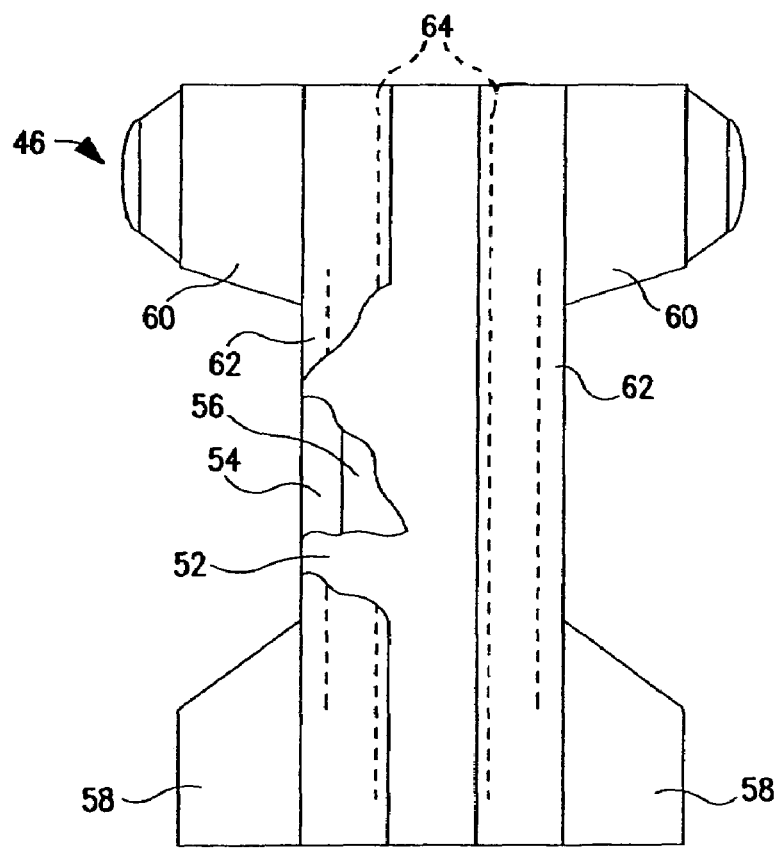

In one aspect, the absorbent core 10 can be incorporated into an absorbent garment. For ease of explanation, the description hereafter will be in terms of the absorbent core 10 incorporated into a diaper 46. As shown in FIG. 5A, a diaper 46 having refastenable sides in a fastened position defines a three-dimensional configuration having a waist opening 48 and a pair of leg openings 50. Referring to FIGS. 5A and 5B, the diaper 46 includes a body-side liner 52 which is configured to contact the wearer, and an outer cover 54 opposite the body-side liner which is configured to contact the wearer's clothing. An absorbent assembly 56 is positioned or disposed between the outer cover 54 and the body-side liner 52. In one embodiment an absorbent core 10 of the invention may be inserted into the diaper as the absorbent assembly 56.

The outer cover 54 desirably includes a material that is substantially liquid impermeable, and can be elastic, stretchable or nonstretchable. The outer cover 54 can be a single layer of liquid impermeable material, but desirably includes a multi-layered laminate structure in which at least one of the layers is liquid impermeable. For instance, the outer cover 54 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., or from National Starch and Chemical Company, Bridgewater, N.J. The liquid permeable outer layer can be any suitable material and desirably one that provides a generally cloth-like texture. One example of such a material is a 20-grams per square meter (gsm) spunbond polypropylene nonwoven web. The outer layer may also be made of those materials of which liquid permeable body-side liner 52 is made. While it is not a necessity for the outer layer to be liquid permeable, it is desired that it provides a relatively cloth-like texture to the wearer.

The inner layer of the outer cover 54 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 54 when a single layer, prevents waste material from wetting articles, such as bedsheets and clothing, as well as the wearer and care giver. A suitable liquid impermeable film for use as a liquid impermeable inner layer, or a single layer liquid impermeable outer cover 54, is a 0.2 millimeter polyethylene film commercially available from Huntsman Packaging of Newport News, Va. If the outer cover 54 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 54. A suitable breathable material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain non-breathable elastic films can also be used to make the outer cover 54. Examples of suitable non-breathable films can be made of styrene-ethylene-butylene-styrene or styrene-isoprene-styrene block copolymers, KRATON polymers from Kraton Polymers of Houston, Tex., metallocene catalyzed elastomers or plastomers, and the like. Other materials suitable for making the outer cover 54 include monolithic breathable films, such as those made of polyether amide based polymers, for example PEBAX from Atofina Chemicals, Inc. of Philadelphia, Pa., and ether/ester polyurethane thermal-plastic elastomers.

The liquid permeable body-side liner 52 is illustrated as overlying the outer cover 54 and absorbent assembly 56, and may but need not have the same dimensions as the outer cover 54. The body-side liner 52 is desirably compliant, soft feeling, and non-irritating to the wearer's skin. Further, the body-side liner 52 can be less hydrophilic than the absorbent assembly 56, to present a relatively dry surface to the wearer and permit liquid to readily penetrate through its thickness.

The body-side liner 52 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body-side liner 52. For example, the body-side liner can be composed of a meltblown or spunbonded web of polyolefin fibers. The body-side liner can also be a bonded-carded web composed of natural and/or synthetic fibers. The body-side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL N-62 available from Uniqema Inc., a division of ICI of New Castle, Del. and GLUCOPON 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body-side liner 52 or can be selectively applied to particular sections of the body-side liner, such as the medial section along the longitudinal centerline.

Non-absorbent structural components in the diaper 46 may include a pair of transversely opposed front side panels 58, and a pair of transversely opposed back side panels 60. The side panels 58, 60 may be integrally formed with the outer cover 54 and/or the body-side liner 52, or may include two or more separate elements.

Other non-absorbent structural components in the diaper 46 may include a pair of containment flaps 62 which are configured to provide a barrier to the transverse flow of any body exudates discharged from the wearer. A flap elastic member 64 may be operatively joined with each containment flap 62 in any suitable manner as is well known in the art. The elasticized containment flaps 62 define an unattached edge that assumes an upright, generally perpendicular configuration in at least a crotch region of the diaper 46 to form a seal against the wearer's body. The containment flaps 62 can be located along transversely opposed side edges of the diaper 46, and can extend longitudinally along the entire length of the training pant or may only extend partially along the length of the diaper. Suitable constructions and arrangements for the containment flaps 62 are generally well known to those skilled in the art.

In another aspect, an absorbent core 10 of the present invention may be used to form an absorbent garment. For example, an absorbent garment may include an absorbent core including a substrate, at least a portion of which is coated with an absorbent adhesive composition, which is folded to provide a plurality of panels at least one of which forms an outer cover of the garment.

Figure 6:
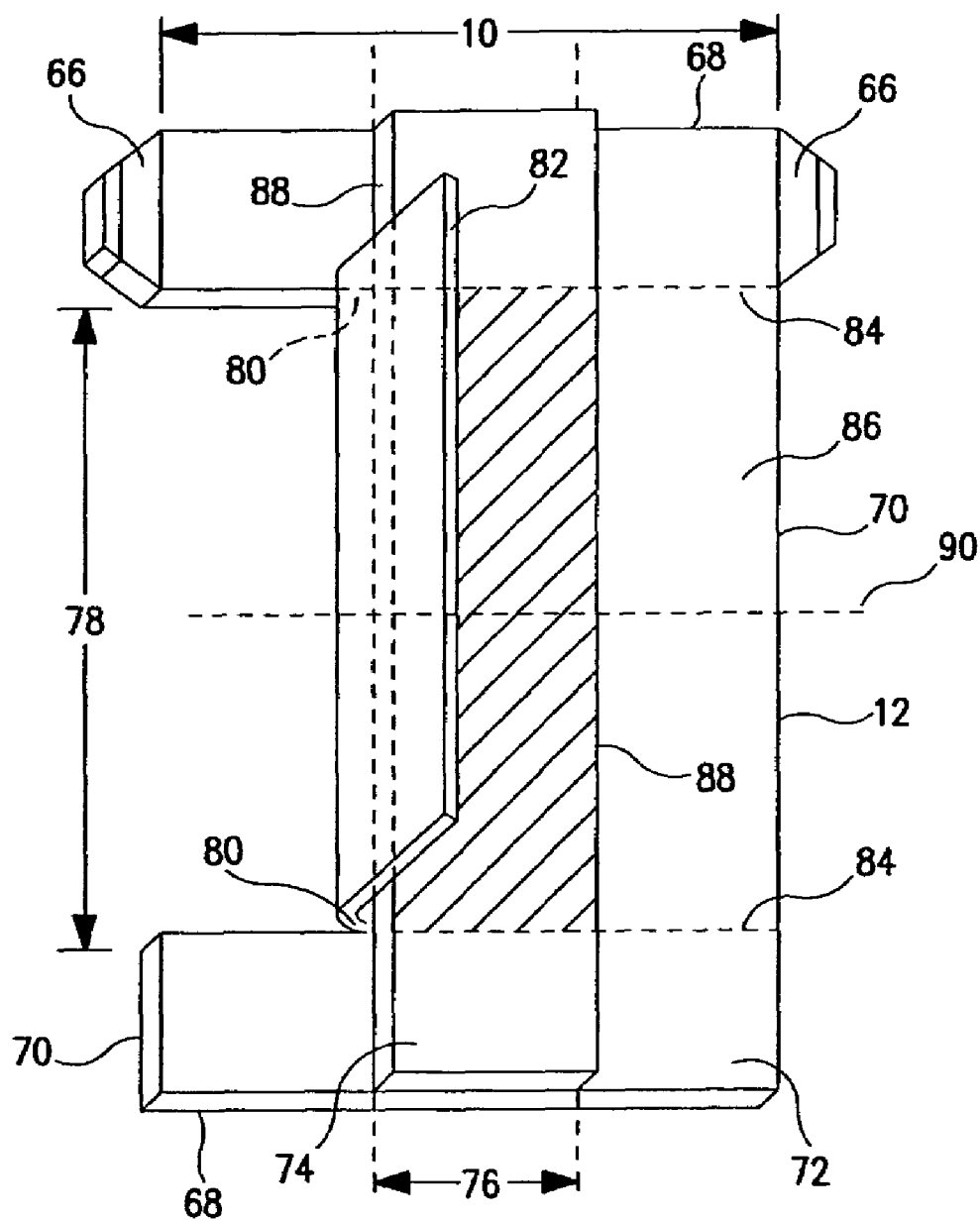
FIG. 6 is a plan view of a diaper formed from an absorbent core of the present invention.

In a specific embodiment, the absorbent core 10 may be used to form a diaper 46. Referring to FIG. 6, a diaper 46 includes an absorbent core 10 and a pair of fastening means 66. The absorbent core 10 includes a substrate 12 having a pair of longitudinal ends 68 and a pair of transverse edges 70. The substrate 12 includes a sheet of a nonwoven material 72, having a width dimension and a length dimension, such as, for example, a 20-gram per square meter (gsm) spunbond polypropylene nonwoven web, at least a portion of which is laminated to a sheet of breathable film 74 such as, for example, a microporous polymer film. Suitably, the breathable film 74 has a length dimension comparable to the length dimension of the nonwoven material and a width dimension that is smaller than the width dimension of the nonwoven material. Advantageously, the breathable film 74 is laminated to the nonwoven sheet 72 in a medial section 76 of the substrate 12. The breathable film 74 may be laminated to the nonwoven sheet 72 by any means known in the art such as, for example, heat embossing, thermal bonding, ultrasonic welding, and/or adhesive lamination.

Desirably, an absorbent adhesive composition is applied to at least a portion of the substrate 12, alternatively to at least a portion of the substrate 12 where the nonwoven sheet 72 is laminated to the breathable film 74, or to at least a central section 78 of the substrate 12 where the nonwoven sheet 72 is laminated to the breathable film 74.

The substrate 12 is slit or cut along a pair of left transverse cutting lines 80 to form a left central section 82 and along a pair of right transverse cutting lines 84 to form a right central section 86. Suitably, the transverse cutting lines 80 and 84 extend from the transverse edges 70 to a pair of longitudinal edges 88 of the medial section 76 of the substrate 12. The substrate 12 is then folded such that the left central section 82 and the right central section 86 overlay the medial section 76 of the substrate 12 thereby enclosing the absorbent adhesive composition within the absorbent core 10. Although the medial section 76, the left central section 82 and the right central section 86 are illustrated in FIG. 6 as having comparable width dimensions, it should be understood that the sections may have any dimension suitable to allow the substrate 12 to be folded in a manner that encloses the absorbent adhesive composition within the absorbent core 10.

As shown in FIG. 6, a pair of fastening means 66 may be provided along each transverse edge 70 of the substrate 12 adjacent one of the longitudinal ends 68. The fastening means 66 may be of any type known in the art such as, for example, tapes, hook and loop fasteners, buttons, snaps and the like. Suitably, the fastening means are refastenable such that the diaper 46 may be opened and closed multiple times while in use. Alternatively, the absorbent core 10 may be folded along a transverse centerline 90 such that the longitudinal ends 68 are placed in a juxtaposed configuration and the transverse edges 70 may be sealed, fused or bonded together to form a 3-dimensional pant. Additional elements such as, for example, waist elastic positioned adjacent the longitudinal ends 68 of absorbent core 10, leg elastics incorporated adjacent longitudinal edges 88 of the medial section 76 of the absorbent core 10, or extensible side panels incorporated along the transverse edges 70 of the absorbent core 10 adjacent the longitudinal ends 68, may be incorporated into the absorbent composite to provide better fit, comfort and leakage protection in use.

Although the diaper 46 illustrated in FIG. 6 has a generally "T"-shaped configuration it is to be understood that other configurations such as an "hour-glass" shape, "trapezoidal" shape or the like may also be achieved using other folding sequence with or without cutting the substrate to form the absorbent core 10. Generally, any shape that may be achieved by folding and optionally cutting the substrate 12 may be used to make an absorbent garment formed from an absorbent composite of the present invention. The absorbent core 10 may be further shaped by molding, pressing, trimming, heating or the like to achieve a desired 2- or 3-dimensional configuration. The absorbent composite 10 may also be embossed or printed to impart desired surface aesthetics.

It is to be understood that although the foregoing description has been drafted in terms of a diaper, the present invention may also be used to form similar absorbent articles such as, for example, training pants, adult incontinence products and garments, feminine hygiene garments, swimwear, and other absorbent garments.

EXAMPLES

Example 1

An absorbent composite of the present invention was prepared as follows. A 3-inch×8-inch (about 7.6 centimeter× 20.3 centimeter) sheet of a breathable film having a basis weight of 0.04 osy (about 1.36 gsm) was placed in a juxtaposed relationship with a 6-inch×8-inch (about 15.2 centimeter×20.3 centimeter) sheet of spunbond material having a basis weight of 0.6 osy (about 20.4 gsm) such that one of the longer edges of the film sheet was positioned adjacent one of the longer edges of the spunbond sheet. The film and spunbond were laminated via heat embossing to provide a substrate including a first panel and a second panel. The first panel included the spunbond material and the second panel included the spunbond/film laminate.

The spunbond side of the second panel was hand-coated with an absorbent crosslinkable binder composition applied uniformly in a concentration of about 100 grams per square centimeter. The crosslinkable binder composition was a copolymer of 57 mole percent acrylic acid, 42 mole percent polyethylene glycol methacrylate, and 1 mole percent methacryloxypropyl trimethoxy silane. The acrylic acid portion of the copolymer was neutralized to 50 percent with sodium hydroxide solution.

The crosslinkable binder composition was prepared as follows. An initiator solution was prepared by dissolving 0.354 grams of benzoyl peroxide in 300 milliliters of ethanol. A monomer solution was prepared by mixing 24.15 grams of acrylic acid (24 mass percent), 73.5 grams of poly(ethylene glycol) methyl ether methacrylate (74 mass percent) and 1.46 grams of 3-(trimethoxysilyl)propyl methacrylate (2 mass percent) in 250 milliliters of ethanol. The initiator solution was heated in a jacketed reactor to 75 degrees Celsius with stirring. The monomer solution was added dropwise to the initiator solution to form a polymerization solution. The polymerization solution was stirred and heated at 75 degrees Celsius for approximately 2 hours after which a solution of 0.096 grams azobisisobutyronitrile (AIBN), dissolved in 30 milliliters of ethanol, was added. The polymerization solution was stirred and heated at 75 degrees Celsius for another hour at which time a second solution of 0.096 grams AIBN in ethanol was added to the polymerization solution. The polymerization solution was stirred and heated at 75 degrees Celsius for an additional hour after which a third addition of 0.096 grams AIBN in ethanol was made. Stirring and heating of the polymerization solution continued at 75 degrees Celsius for an additional time to reach a total reaction time of about 7 hours. The reactor was cooled to 20 degrees Celsius and the resulting polymer solution was stirred in a nitrogen atmosphere overnight to provide a binder polymer designated binder polymer 1a. A portion of the polymer solution was dried for 16 hours at room temperature to create a sticky, crosslinked water-absorbent film. The polymer concentration of the polymer solution was 16.2 percent by weight.

A portion of the polymer solution was treated with sodium hydroxide solution to neutralize a portion (50 percent) of the acrylic acid units in the binder polymer 1a in order to increase the absorbency of the crosslinked film generated by drying the polymer solution. The neutralization was done by adding 5.25 grams of 48.5 percent sodium hydroxide solution to 236 grams of polymer solution (16.2 percent polymer) and stirring at room temperature for 5 minutes.

The first panel of the substrate was folded over the second panel thereby enclosing the absorbent crosslinkable binder composition between the two panels. The folded substrate was placed on the bottom plate of a flat Carver press, Model 25-15HC (Catalog No. 3977) available from Fred S. Carver, Inc., Wabash, Ind. Shims having a thickness of 0.9 millimeters were also placed on the bottom plate of the Carver press to provide gap-stops. Accordingly, when the top and bottom plates of the Carver press were brought together the top plate contacted the shims and a 0.9-millimeter gap was formed between the two plates. The folded substrate was compressed for 10 seconds with a force of 10,000 pounds (44,450 Newtons) at room temperature (approximately 73° F. or 23° C.) to provide an absorbent composite of the present invention having a "u"-shaped cross-section and a thickness of about 0.9 millimeters.

Example 2

An absorbent composite of the present invention was prepared as in Example 1 except prior to folding the first panel over the second panel a piece of tissue web was placed over the coated portion of the second panel. The tissue web was prepared using the Uncreped Through-Air Dried (UC-TAD) process as described in U.S. Pat. Nos. 5,656,132 and 5,932,068 to Farrington, Jr., et al., and had a basis weight of 50 grams per square meter. The first panel was then folded over the second panel thereby enclosing the absorbent crosslinkable binder composition and the UCTAD sheet between the two panels. After compression, the resulting absorbent composite had a "u"-shaped cross-section and a thickness of about 1.4 millimeters.

Example 3

An absorbent composite of the present invention was prepared as follows. A 3-inch×8-inch (about 7.6 centimeter× 20.3 centimeter) sheet of a breathable film having a basis weight of 0.04 osy (about 1.36 gsm) was placed in a juxtaposed relationship with a 9-inch×8-inch (about 22.9 centimeter×20.3 centimeter) sheet of spunbond material having a basis weight of 0.6 osy (about 20.4 gsm) such that the film sheet was positioned adjacent a medial 3-inch×8-inch (about 7.6 centimeter×20.3 centimeter) section of the spunbond sheet. The film and spunbond were laminated via heat embossing to provide a substrate including a first panel, a second panel, and a third panel having approximately equal dimensions. The first panel included spunbond material, the second panel included the spunbond/film laminate and the third panel included spunbond material.

The second panel was coated with the absorbent crosslinkable binder composition as disclosed in Example 1. The first panel was sprayed with a surfactant mixture including AHCOVEL N-62 available from Uniqema Inc., a division of ICI of New Castle, Del., U.S.A. and GLUCO-PON 220UP available from Cognis Corporation of Ambler, Pa., and produced in Cincinnati, Ohio, in an active ratio of 3:1. The surfactant was applied at a concentration of about 0.45 weight percent based on the total weight of surfactant and the spunbond material of the first panel.

The first panel was folded over the second panel thereby enclosing the absorbent crosslinkable binder composition and the surfactant between the first and second panels. The third panel was then folded over the first panel and the folded substrate was placed on the bottom plate of a Carver press. Shims having a thickness of 1.2 millimeters were also placed on the bottom plate of the Carver press to provide gap-stops. The folded substrate was compressed as in Example 1 to provide an absorbent composite of the present invention having an "e"-shaped cross-section and a thickness of about 1.2 millimeters.

Example 4

A feminine hygiene product of the present invention was formed using the absorbent composite of Example 1 as follows. Three strips of a moisture-insensitive adhesive were applied to the film side of the second panel at a concentration of about 5 to about 10 grams per square centimeter, and were covered by an adhesive releasable paper. The moisture-insensitive adhesive was NS-34-5561 available from National Starch and Chemical Company of Bridgewater, N.J. The absorbent composite was die-cut into a dumbbell shape to form a feminine hygiene product.

Example 5

A piece of surge material made according to U.S. Pat. No. 5,364,382 to Latimer et al., manufactured by Kimberly-Clark was coated with a mixture of 8.7 grams superabsorbent material and 19.3 grams of a crosslinkable binder composition in 15 percent w/w ethanol. The surge material had a basis weight of 1.5 osy (about 50.9 gsm). The superabsorbent material was FAVOR SXM 9543, available from Stockhausen Inc., located in Greensboro, S.C. The crosslinkable binder composition was a copolymer of 70 mole percent acrylic acid, 29 mole percent polyethylene glycol methacrylate, and 1 mole percent methacryloxypropyl trimethoxy silane. The acrylic acid portion of the copolymer was neutralized to 70 percent with sodium hydroxide solution.

The coating was applied with a spatula onto the medial 3-inch×12-inch (about 7.6 centimeter×30.5 centimeter) region of a 9-inch×12-inch (about 22.9 centimeter×30.5 centimeter) sheet of surge material. The coated surge material was placed in a fume hood at room temperature to evaporate the ethanol. After the ethanol had evaporated, the surge material was folded as illustrated in FIGS. 3A through 3C to provide an absorbent composite of the present invention having an "e"-shaped cross-section that provides both fluid intake and retention functionality.

Example 6

An absorbent composite of the present invention was prepared as in Example 5 except one of the side sections of the surge material was folded over the coated medial section of the surge material prior to evaporating the ethanol. The ethanol was then evaporated in order to set the binder composition and to adhere the first side section to the absorbent crosslinkable binder composition to provide more intimate contact between the coated and uncoated sections. The second side section was then folded over the first side section to provide an absorbent composite of the present invention having an "e"-shaped cross-section.

Example 7

An absorbent composite including a multifunctional substrate was prepared as follows. A multifunctional substrate was prepared by placing a first 3-inch×12-inch (about 7.6 centimeter×30.5 centimeter) section of a 9-inch×12-inch (about 22.9 centimeter×30.5 centimeter) sheet of surge material as in Example 5 on the bottom plate of a Carver press. Shims having a thickness of 0.5 millimeters were also placed on the bottom plate of the Carver press to provide gap-stops. The top and bottom plates of the Carver press were heated to about 220° F. (about 105° C.). The first section of the surge material was compressed between the top and bottom plates for 60 seconds with a force of 10,000 pounds (44,450 Newtons) to increase the density of the first section of the surge material. The compressed first section of the surge material had a density approximately twice that of the uncompressed remainder of the sheet.

A coating of an absorbent crosslinkable binder composition and superabsorbent material as in Example 5 Was then applied to a medial 3-inch×12-inch (about 7.6 centimeter× 30.5 centimeter) section of the surge material. The surge material was then folded as illustrated in FIGS. 3A through 3C such that the densified first section of the surge material was positioned adjacent the coated medial section of the sage material and the undensified, uncoated section of the surge material was positioned adjacent the densified first section of the surge material to form an absorbent composite having an "e"-shaped cross-section. The resulting absorbent composite provides intake, distribution, and retention functionality.

Example 8

An absorbent composite including a multifunctional substrate was prepared as follows. A multifunctional substrate was prepared as in Example 7. Similar to Example 6, a medial section of the surge material was coated with the absorbent cross-linkable binder composition and superabsorbent material of Example 5 and the densified section of the surge material was folded over the coated medial section prior to evaporating the ethanol. After the ethanol was evaporated the undensified section of the surge material was folded over the densified section of the surge material to form an absorbent composite of the present invention having an "e"-shaped cross-section.

Test Method for Determining Absorbent Capacity

Centrifuge Retention Capacity: The Centrifuge Retention Capacity (CRC) is a test which measures the amount-in grams of a test liquid, such as water or a 0.9 weight percent solution of sodium chloride in distilled water, that a gram of a material can absorb or immobilize in a single time interval, or a series of time intervals, after being subjected to a centrifugal force for a period of time.

Stock teabag material is cut into a 3-inch (about 7.6 centimeters) by 5-inch (about 12.7 centimeters) rectangle and folded in half to form a 2.5-inch (about 6.4 centimeters) by 3-inch (about 7.6 centimeters) rectangle with the sealable face inward. Two of the three open sides are heat sealed with the inside edge of the seal about 0.25 inch (about 0.64 centimeter) from the edge. About 0.2 gram of sample material (or a 1-inch by 1-inch square piece of composite) is placed into a preweighed teabag, and the open end of the teabag is heat sealed. The teabag is submerged in a pan of test liquid for a time interval, removed, allowed to drain on a wire mesh at about a 45 degree angle for about 2 minutes, centrifuged for about 3 minutes at 290 times the gravitational force and then weighed. If a series of time intervals is to be run, the sample is returned to the test liquid until the next time interval. After each time interval, the teabag is again allowed to drain on the wire mesh for about 2 minutes, again centrifuged for about 3 minutes at 290 times the gravitational force, and then weighed again. After the final time interval, the teabag is then allowed to dry and then weighed again. A blank test is also run by centrifuging, under similar conditions, an empty teabag that had also been placed in the test liquid. The weight of the test liquid retained per gram of dry sample material after centrifuging is calculated from the data obtained, and this is expressed as the Centrifuge Retention Capacity value in terms of grams of test liquid retained per gram of dry sample material.

Test Method for Determining Absorbency under Load for Composites (AULC)

The Absorbency Under Load for Composites (AULC) is a test that measures the ability of an absorbent material to absorb a liquid (such as a 0.9 weight percent aqueous solution of sodium chloride) while under an applied load or restraining force. The AULC method provides a slight positive head of fluid for the absorbent material, which is allowed to swell under a restraining load. The material is drained under vacuum at the end of the test.

The AULC test cup is cylindrical with a height of at least 1.75 inches; the inner diameter describes a cylinder, the base of which has an area of 4.37 in$^2$. The bottom of the test cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder. A spacer weighing about 60 grams and having a circular diameter of about 2.36 inches is made to fit within the AULC test cup without binding. The spacer is formed with multiple cylinder holes of about 9 mm diameter, providing an open area of about 52 percent. A 100 mesh screen is adhered to the bottom of the spacer in a similar manner to that of mesh that is attached to the bottom of the test cup or other suitable method. Weights are sized to fit on top of the spacer. The first weight should apply a load of 600 grams (in combination with the spacer), and the second weight, in combination with the first weight and the spacer disc, should apply a load of 1800 grams.

Additional equipment required includes a vacuum trap for liquid that is suctioned out of the composite material at the end of the test, shallow dishes such as Petri dishes or plastic weighing boats suitable for holding an excess amount of liquid than will be imbibed by the sample, and a thin mesh screen with a thickness between 0.3 mm and 0.75 mm and a mesh size of about 1.2 mm. The vacuum trap is adapted to apply vacuum to an area matching the dimensions of the bottom of the AULC testing cup (for example, a larger vacuum area may be selectively screened with a relatively impermeable material except in an area matching the dimensions of the bottom of the AULC cup). The vacuum applied is about 27 inches of mercury.

Composite samples are cut to fit inside the AULC testing cup. Airlaid or nonwoven-based materials are cut into circles 2.35 inches in diameter. Airformed samples are cut or formed into circles, each with a diameter of 2.312 inches.

To carry out the test, test cup and spacer should be clean and dry. The test cup and spacer to be used in each trial should be weighed together (Measurement 1), and the mass recorded. The specimen is placed in the sample cup and the spacer is placed on top of the sample in the cup. The assembly is then weighed (Measurement 2), and the mass is recorded. The appropriate amount of weight is placed atop the spacer, if required. The spacer alone applies a force of 0.03 pounds per square inch of area (psia; the disc and first weight, with a net mass of 600 grams, apply a force of 0.3 psi, and the disc and both weights together, having a net mass of 1800 grams, apply a force of 0.9 psi).

The cup holding the specimen is placed in a pool of excess fluid in the shallow dish on top of the mesh screen and a one hour timer is started immediately. The level of fluid in the dish is maintained between about 1 mm and 2 mm depth. Following one hour, the specimen is removed from the fluid bath. Any fluid that may have accumulated atop the specimen should be poured off without displacing any weights atop the spacer disc. The specimen assembly is then placed on the vacuum box, with any weights still in place. Vacuum is applied to the sample for 30 seconds.

Any weights atop the spacer are then removed from the assembly and the assembly is weighed again (Measurement 3). The mass is recorded.

The dry weight of the specimen is calculated by subtracting Measurement 1 from Measurement 2. The amount of fluid absorbed by the specimen is calculated by subtracting Measurement 2 from Measurement 3. The absorbency under load of the composite material is calculated as the amount of fluid absorbed divided by the dry weight of the specimen.

At least three specimens of each sample should be measured, and the absorbency under load values should be averaged to obtain an overall absorbency under load for the composite sample.

Test for Determining Tensile Strength

The tensile strength can be measured using the Strip Tensile Test Method described in U.S. Statutory Invention Registration No. H1,969 issued to Fell on 5 Jun. 2001.

Test for Determining Thickness

All measurements of composite thickness were done at a pressure of 0.05 psi (0.34 kPascals) with a Mitutoyo Digimatic Indicator (Type IDF 150E), available from Mitutoyo American Corporation of Aurora, Ill., equipped with a "foot" composed of a plastic disk having a diameter of 3 inches (7.6 centimeters) and a weight of 78.5 grams. The instrument is zeroed with the foot in contact with the baseplate. A sample is placed on the baseplate and the foot is lowered onto the sample until a load of 0.05 psi (0.34 kPascals) is applied. The thickness of the sample is then measured to the nearest 0.01 millimeter.

Test Method for Determining Stiffness

A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester, Model 4171-E, manufactured by Teledyne Gurley, a business having offices in Troy, N.Y. For purposes of the present invention, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent core, comprising:
   a substrate which is folded upon itself to provide a plurality of panels, wherein the substrate is folded to provide an absorbent core having a cross-sectional configuration selected from the group consisting of an "e"-shape, a "z"-shape, a sigma-shape and an accordion-shape;
   the substrate performing a first fluid handling function;
   at least one portion of at least one panel performing a second fluid handling function different from the first fluid handling function;
   wherein the at least one portion of at least one panel further comprises a modifying material comprising a binding agent which is an absorbent adhesive composition of a crosslinkable binder composition; and
   the crosslinkable binder composition comprises an alkoxysilane grafted poly(ethylene oxide).

2. The absorbent core of claim 1, wherein the substrate comprises a material selected from the group consisting of nonwoven webs, woven webs, knitted fabrics, cellulosic tissue sheets, plastic films, foams, stranded composites, elastomer net composites and combinations thereof.

3. The absorbent core of claim 1, wherein the first and second fluid handling functions are selected from the group consisting of body waste barrier, distribution, feces containment, feces modification, intake, lock-up, menses containment, menses modification, odor control, retention, and skin treatment.

4. The absorbent core of claim 1, wherein the at least one portion of at least one panel comprises apertures.

5. The absorbent core of claim 1, wherein the at least one portion of at least one panel has a higher density than another portion of the substrate.

6. The absorbent core of claim 1, wherein the substrate is folded such that at least a portion of the modifying material is enclosed within the absorbent core.

7. The absorbent core of claim 1, wherein the modifying material comprises a viscoelastant.

8. The absorbent core of claim 1, wherein the modifying material comprises a surfactant.

9. The absorbent core of claim 1, wherein the modifying material comprises a binding agent which is an absorbent adhesive composition of an in situ neutralizable binder composition.

10. The absorbent core of claim 9, wherein tho in situ neutralizable binder composition includes a copolymer of an unneutralized polyacid and a polyamine binder material.

11. The absorbent core of claim 10, wherein the copolymer of an unneutralized polyacid comprises a material selected from the group consisting of poly(acrylic acid), poly(methacrylic acid), poly(maleic acid), carboxymethyl cellulose, alginic acid, poly(aspartic acid), and poly(glutamic acid).

12. The absorbent core of claim 10, wherein the polyamine binder material comprises a material selected from the e group consisting of poly(vinylamine) a polyethylenimine, a poly(vinylguanidine), a poly(allylamine), a poly(allylguanidine), a poly(lysine), a poly(arginine), poly (histidine), a poly(dialkylaminoalkyl (meth)acrylamide), and copolymers containing lysine, arginine or histidine.

13. The absorbent core of claim 10, wherein the substrate is folded such that the copolymer of an unneutralized polyacid and the polyamine binder material are brought together to provide a macro bipolar absorbent film.

14. The absorbent core of claim 1, wherein the modifying material comprises a binding agent which is an absorbent adhesive composition of an in situ polymerizable binder composition.

15. The absorbent core of claim 1, wherein the crosslinkable binder composition has a glass transition temperature of 30 degrees Celsius or lower.

16. The absorbent core of claim 1, wherein the crosslinkable binder composition comprises, an acrylic acid copolymer selected from the group consisting of acrylic acid and long chain, hydrophilic acrylate esters, acrylic acid and long chain, hydrophilic methacrylate esters, and acrylic acid salts and long chain, hydrophilic methacrylate esters.

17. The absorbent core of claim 1, further comprising an absorbent material having an absorbent capacity of at least about 7 grams 0.9 weight percent saline per grain absorbent material.

18. The absorbent core of claim 17, wherein the absorbent material comprises a superabsorbent material selected from the group consisting of crosslinked forms of sodium polyacrylate, sodium polymethacrylate, polyacrylamide, carboxymethyl cellulose, grafted starch, poly(sodium aspartate), poly(vinyl amine), poly(dimethyldiallyl amine), chitosan salt, and/or poly(ethylene imine) and combinations thereof.

19. The absorbent core of claim 17, further comprising an attachment mechanism for securing the absorbent material to the substrate, the attachment mechanism selected from the group consisting of physical bonds, chemical bonds and combinations thereof.

20. The absorbent core of claim 1, wherein the crosslinkable binder includes about 0.1 to about 20 weight percent of monomer to weight of poly(ethylene)oxide.

21. The absorbent core of claim 20, wherein the monomer comprises a trialkoxy silane functional group.

22. The absorbent core of claim 20, wherein the monomer is selected from the group consisting of methacryloxyethyl trimethoxy silano, methacryloxypropyl triethoxy silane, methacryloxypropyl tripropoxy silane, acryloxypropylmethyl dimethoxy silane, 3-acryloxypropyl trimethoxy silane, 3-methacryloxyproplmethyl diethoxy silane, 3-methacryloxyproplmethyl dimethoxy silane, 3-methacryloxypropyl tris(methoxyethoxy) silane and combinations thereof.

23. The absorbent core of claim 20, wherein the crosslinkable binder comprises poly(ethylene glycol) methacrylate having from 1 to 13 ethylene glycol units.

24. An absorbent article comprising an absorbent core having a substrate which is folded upon itself to provide a plurality of panels; wherein the substrate is folded to provide an absorbent core having a cross-sectional configuration selected from the group consisting of a "z"-shape, a sigma-shape and an accordion-shape;

the substrate performing a first fluid handling function;

at least one portion of at least one panel performing a second fluid handling function different from the first fluid handling function;

wherein the at least one portion of at least one panel further comprises a modifying material comprising a binding agent which is an absorbent adhesive composition of a crosslinkable binder composition; and the crosslinkable binder composition comprises an alkoxysilane grafted poly(ethylene oxide).

25. The absorbent article of claim 24, wherein the article is an absorbent garment.

26. The absorbent article of claim 25, wherein the absorbent garment comprises:

a bodyside liner;

a garment-side cover; and the absorbent core positioned between the bodyside liner and the garment-side cover.

27. The absorbent article of claim 25, wherein the absorbent garment has an average thickness of about 6.4 millimeters or less.

28. The absorbent article of claim 24, wherein the article is a medical garment.

29. The absorbent article of claim 24, wherein the article is selected from the group consisting of wipes, tissues, sweat pads, head mats and bed pads.

* * * * *